United States Patent [19]
Brewer et al.

[11] Patent Number: 6,134,479
[45] Date of Patent: Oct. 17, 2000

[54] ELECTRODE TRIAD FOR EXTERNAL DEFIBRILLATION

[75] Inventors: James E. Brewer, Minneapolis, Minn.; Charles D. Swerdlow, Los Angeles, Calif.; Kenneth F. Olson, Edina, Minn.

[73] Assignee: SurVivaLink Corporation, Minneapolis, Minn.

[21] Appl. No.: 09/243,579

[22] Filed: Feb. 3, 1999

Related U.S. Application Data

[60] Provisional application No. 60/092,185, Jul. 9, 1998.

[51] Int. Cl.$^7$ ............................................. A61N 1/04
[52] U.S. Cl. ................................. 607/142; 607/5
[58] Field of Search ................... 607/5, 67, 142, 607/115, 152, 148

[56] References Cited

U.S. PATENT DOCUMENTS

| | | | |
|---|---|---|---|
| 4,381,789 | 5/1983 | Naser et al. | 607/67 |
| 5,928,270 | 7/1999 | Ramsey, III | 607/5 |

*Primary Examiner*—George R. Evanisko
*Attorney, Agent, or Firm*—Patterson, Thuente & Skaar, P.A.

[57] ABSTRACT

An energy delivery system for use with an automatic external defibrillator (AED), the AED having a case containing a plurality of AED components, a battery electrically coupled to a control system, the control system communicatively coupled to a charge system, the charge system for generating a stored quantity of energy responsive to a communication from the control system, the control system selectively commanding a discharge of the stored energy to an electrical connector, the energy delivery system includes three electrodes, each electrode for making electrical contact with a skin surface of a patient, each electrode being in electrical contact with the electrical connector for communicating the stored energy to the patient. A method of defibrillating the heart of a patient using an AED, the AED having electrical energy discharge circuitry for generating a defibrillating energy discharge to affect the heart of the patient, the heart being in a state of fibrillation, includes the steps of placing three electrodes on the person of a patient to define a desired electrical path and discharging electrical energy across the electrical path.

3 Claims, 9 Drawing Sheets

ELECTRODE TRIAD FOR EXTERNAL DEFIBRILLATION

RELATED APPLICATIONS

The present application claims the benefit of U.S. Provisional Application No. 60/092,185 filed Jul. 9, 1998, incorporated herein by reference.

TECHNICAL FIELD

The present invention relates generally to external defibrillators used to treat sudden cardiac arrest. More particularly, the present invention relates to defibrillation electrodes for use with automatic external defibrillators (AEDs).

BACKGROUND OF THE INVENTION

Cardiac-arrest, exposure to high voltage power lines, and other trauma to the body can result in ventricular fibrillation. Ventricular fibrillation is the rapid and uncoordinated contraction of the myocardium of the heart. The use of external defibrillators to restore the heart beat to its normal pace through the application of an electrical shock is a well recognized and important tool in resuscitating patients. External defibrillation is typically used in emergency settings in which the patient is unconscious.

Automatic External Defibrillators (AEDs) are used by first responders such as police officers, fire fighters, and emergency medical technicians to resuscitate victims of sudden cardiac arrest. Studies have shown that the chances of successfully resuscitating a patient decrease approximately ten percent per minute following the onset of sudden cardiac arrest. Accordingly, a victim of sudden cardiac arrest will most likely not survive unless a trained rescuer responds in less than ten minutes after the cardiac arrest occurs and successfully defibrillates the heart.

Automatic External Defibrillators are designed to be very easy to use so that rescuers without extensive medical backgrounds can successfully resuscitate victims of sudden cardiac arrest. AEDs are currently being carried in emergency vehicles such as police cars, paramedic vehicles, and fire trucks. AEDs are also being widely deployed in areas where large numbers of people gather, such as at sports stadiums, gambling casinos, etc.

Because AEDs are portable devices for use in field locations, it is preferred that they be small and light weight. Because the AED is used in emergency situations far (e.g. more than ten minute travel time) from medical care facilities, the electo-therapy delivered by the AED must be effective at stopping ventricular fibrillation and returning the heart to a normal rhythm. It is desirable to lower electrical impedance across the patient and also to ensure an energy path that passes through the patient's heart. Current AEDs use two electrodes. See FIGS. 4 and 6. Two electrodes result in higher than desired patient impedance and make it difficult to establish an energy path that passes through the patient's heart.

SUMMARY OF THE INVENTION

The AED of the present invention has the following advantages as compared with existing devices. The electrical impedance across the patient is lower when the electrode triad of the present invention is used as compared to using only the two electrodes of the prior art devices. Lowering electrical impedance while ensuring a current path through the heart greatly improves the ability of the AED to defibrillate a patient by raising peak and average currents for a shock pulse having any given energy level.

Further, the electrode triad directs the flow of defibrillation current in a way which improves the ability of AED to defibrillate a patient, as described in relation to the shock vector indicated below. An AED designed for use with the electrode triad may be smaller and lighter. Since the ability to defibrillate a patient is improved by the use of the electrode triad, the AED does not need to deliver as much energy in order to ensure adequate defibrillation current to the patient. When the AED does not need to deliver as much energy in order to effect defibrillation, it can be made smaller and lighter.

Additionally, in one preferred embodiment, the electrical connector associated with the electrode triad has only two electrical contacts, making it compatible with existing AEDs that employ only two electrodes. The electrode triad can therefore be retrofitted to existing AED's without modification of the AED.

The three electrodes of the triad are packaged in a way which will allows them to be used exactly like a standard pair of electrodes, if so desired. Alternately, the three electrodes of the triad can also be used in the inventive electrode triad configuration.

The present invention is an energy delivery system for use with an automatic external defibrillator (AED), the AED having a case containing a plurality of AED components, including a battery electrically coupled to a control system, the control system communicatively coupled to a charge system, the charge system for generating a stored quantity of energy responsive to a communication from the control system, the control system selectively commanding a discharge of the stored energy to an electrical connector, the energy delivery system includes three electrodes, each electrode for making electrical contact with a skin surface of a patient, each electrode being in electrical contact with the electrical connector for communicating the stored energy to the patient.

The present invention is further a method of defibrillating the heart of a patient using an AED, the AED having electrical energy discharge circuitry for generating a defibrillating energy discharge to affect the heart of the patient, the heart being in a state of fibrillation, includes the steps of placing three electrodes on the person of a patient to define a desired electrical path and discharging electrical energy across the electrical path.

DETAILED DESCRIPTION OF THE DRAWINGS

Figure 1:
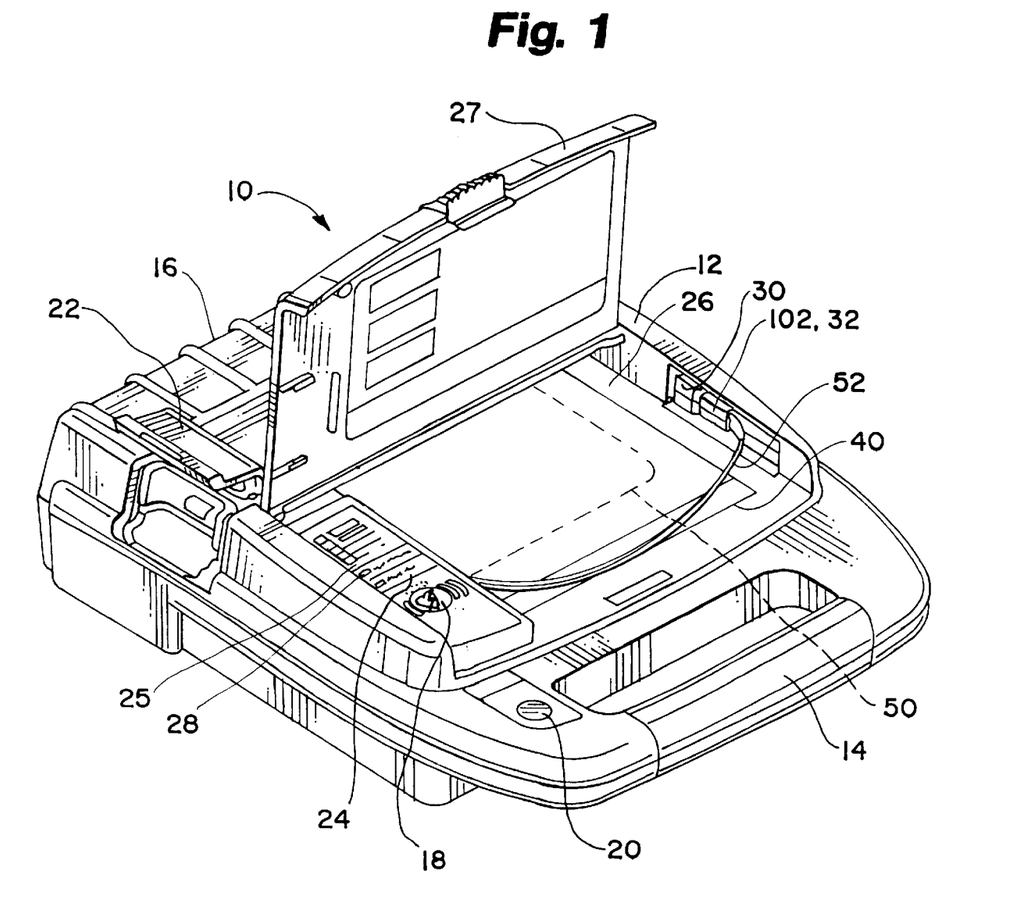
FIG. 1 is a perspective view of an automatic external defibrillator (AED) of the present invention.

The AED of the present invention is shown generally at 10 in FIG. 1. AED 10 includes case 12 with carrying handle 14 and battery pack 16, which is removably disposed within a battery compartment (not shown) defined in case 12. Battery pack 16 functions as an energy source for AED 10. Visual maintenance indicator 20 and data access door 22 are located on the outside of case 12 to facilitate access by the operator. Case 12 also includes panel 24 and has electrode compartment 26 defined in a top portion thereof. Panel 24 includes illuminable resume/rescue switch 18 and diagnostic display panel 25 with "electrodes" indicator light 28. Panel 24 and electrode compartment 26 are enclosed by selectively closeable lid 27.

Electrode compartment 26 contains AED electrode connector 30 and electrode pouch 40. In the prior art, electrode pouch 40 hermetically encloses a pair of electrodes 50. A similar electrode pouch 40 contains the electrode triad 100 of the present invention, as indicated below. Electrodes 50 are removably connected to AED electrode connector 30 by connector 32 coupled at the terminus of leads 52. Connectors 30, 32 are typically configured with two connectors, one connector for connecting to a first electrode 50 and the second connector for connecting to a second electrode 50. Electrodes 50 are attached to a patient prior to a rescue intervention procedure with AED 10, as indicated below.

AED 10 also includes a digital microprocessor-based electrical control system (not shown) for controlling overall operation of AED 10 and for delivering a defibrillation shock pulse through electrodes 50 via AED connector 30, electrode connector 32, and leads 52. The electrical control system further includes an impedance measuring circuit for testing the interconnection and operability of electrodes 50 in order to detect several electrode faults. For example, if the conductive hydrogel adhesive on electrodes 50 is too dry or if electrodes 50 are not properly connected to electrode connector 32 a relatively high impedance (e.g. greater than about 20 ohms) will be present across the two connectors of electrode connector 32. However, when fresh electrodes 50 are properly packaged, the impedance across the two connectors of electrode connector 32 will be between about 2 and 1–0 ohms.

To insure operable electrodes, an electrode self-test is conducted (e.g., daily or upon opening lid 27) in which the interconnection and operability of electrodes 50 are checked with the impedance measuring circuit. If electrodes 50 are missing or unplugged from connector 30, if electrodes 50 are damaged, or if the conductive hydrogel adhesive on electrodes 50 is too dry, the control system of AED 10 will illuminate "Electrodes" indicator light 28 on diagnostic display panel 25.

Figure 2:
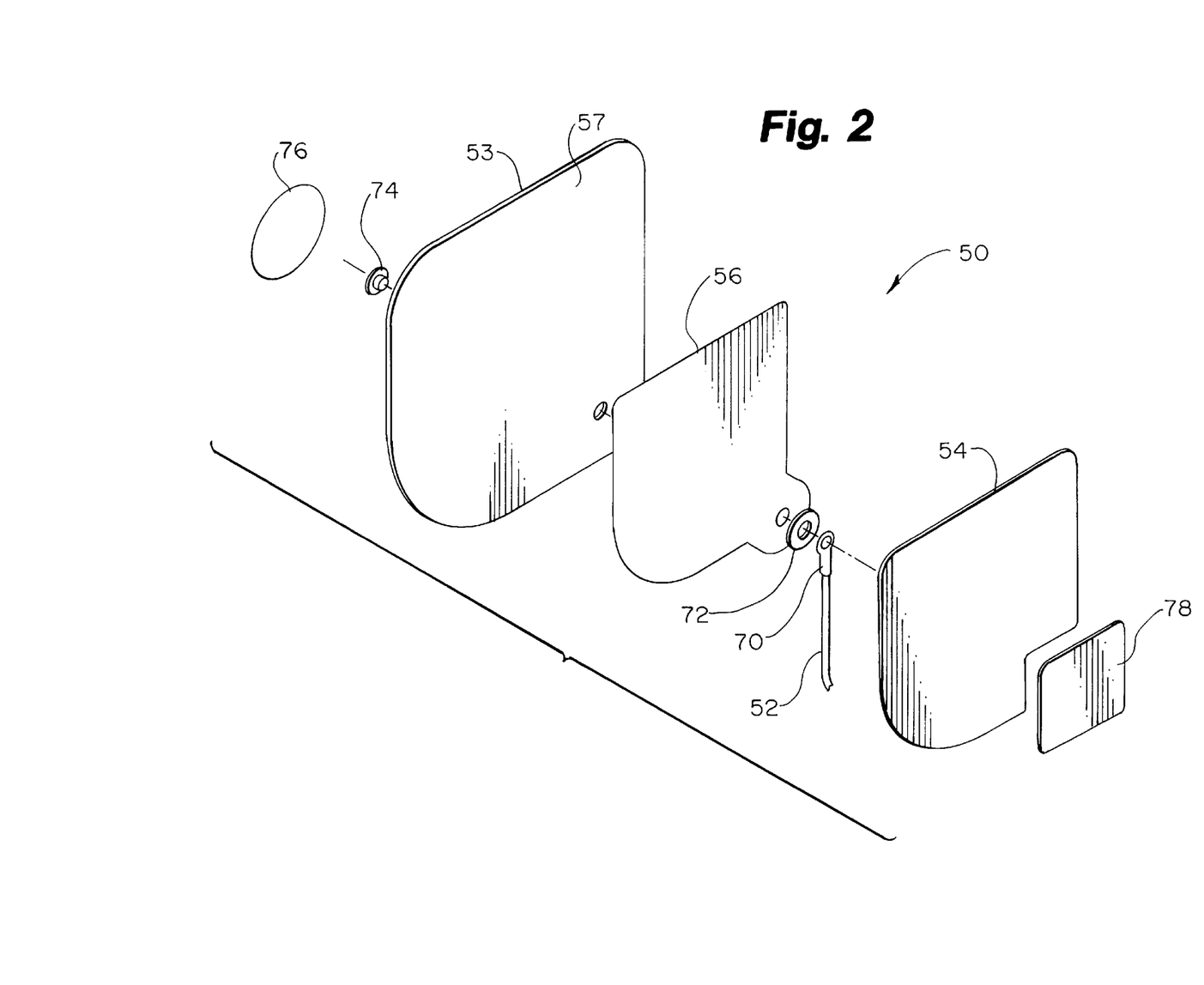
FIG. 2 is an exploded, perspective view of a defibrillation electrode of the present invention.

FIG. 2 is an exploded view of an electrode 50. Electrode 50 includes flexible, adhesive coated backing layer 53 (preferably a polymeric foam), and patient engaging layer 54. Patient engaging layer 54 is preferably a hydrogel material which has adhesive properties, and which is electrically conductive. Hydrogel adhesive of this type is commercially available from LecTec Corporation (Minnetonka, Minn.) and Tyco International Ltd. (Hamilton, Bermuda). Current dispersing flexible conductive portion 56 is preferably located between backing layer 53 and patient-engaging hydrogel layer 54. Conductive portion 56, as shown, need not be the same size as backing layer 53 and is preferably a homogeneous, solid, thinly deposited metallic substance, or a conductive ink.

An adhesive coated border 57 is formed by a portion of adhesive coated backing layer 53. This adhesive coated border extends about conductive portion 56 and patient engaging hydrogel layer 54. Insulated lead wire 52 is terminated with a wire terminal 70. Wire terminal 70 is electrically connected to conductive portion 56 via conductive rivet 74 and washer 72. Conductive rivet 74 is covered on a first side with insulating disk 76. Conductive rivet 74, washer 72, and wire terminal 70 are all covered on a second side with insulating pad 78.

Further examples of electrode pad construction for use with AED 10 are described and shown in U.S. Pat. Nos. 5,697,955, 5,579,919, and 5,402,884, all hereby incorporated by reference.

Figure 3:
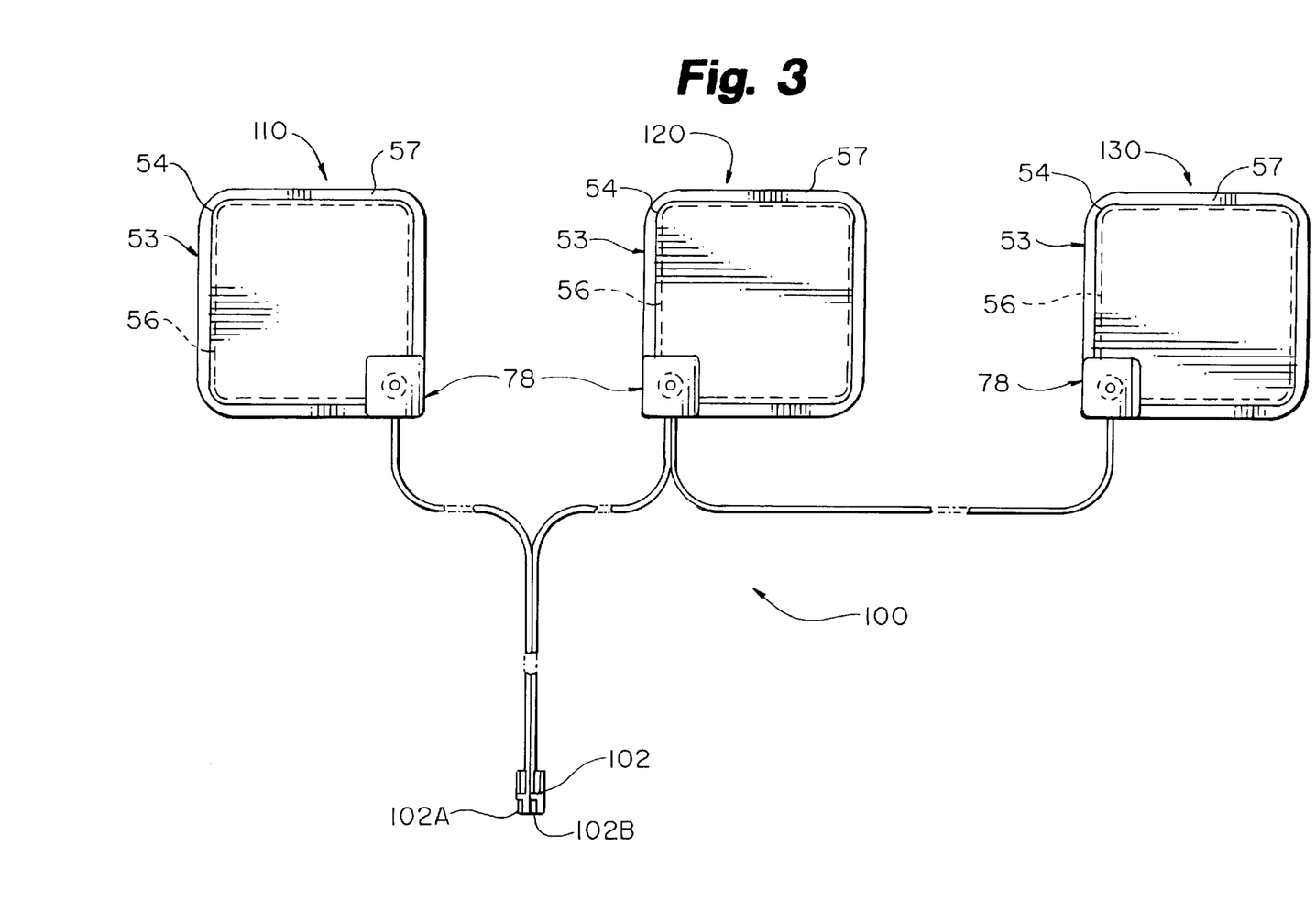
FIG. 3 is a plan view of the electrode triad of the present invention.

Referring to FIG. 3, the electrode triad 100 of the present invention includes an electrode connector 102 which mates with AED electrode connector 30 of AED 10. Electrode connector 102 is substantially similar to electrode connector 32, described above. Electrical connector 102 includes two electrical contacts 102A and 102B. Triad 100 is designed to replace the prior art electrodes 50 in the AED 10 and to couple to the two connectors of electrode connector 32 without modification of the existing AED 10.

Figure 5:
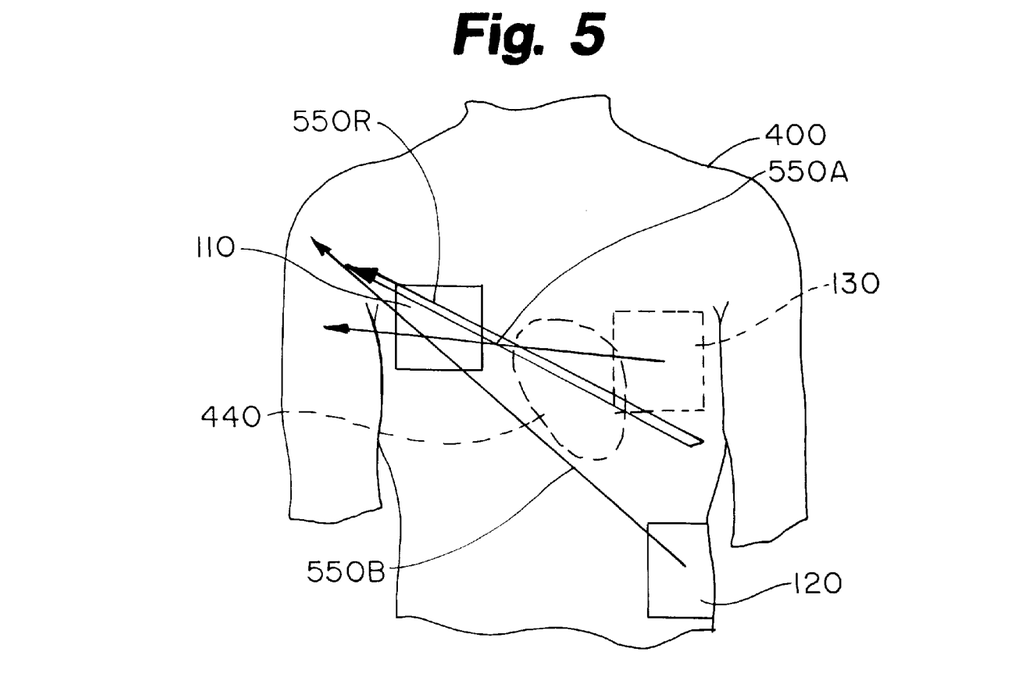
FIG. 5 is a plan view of a human chest with the electrode triad of the present invention applied thereto.
Figure 12:
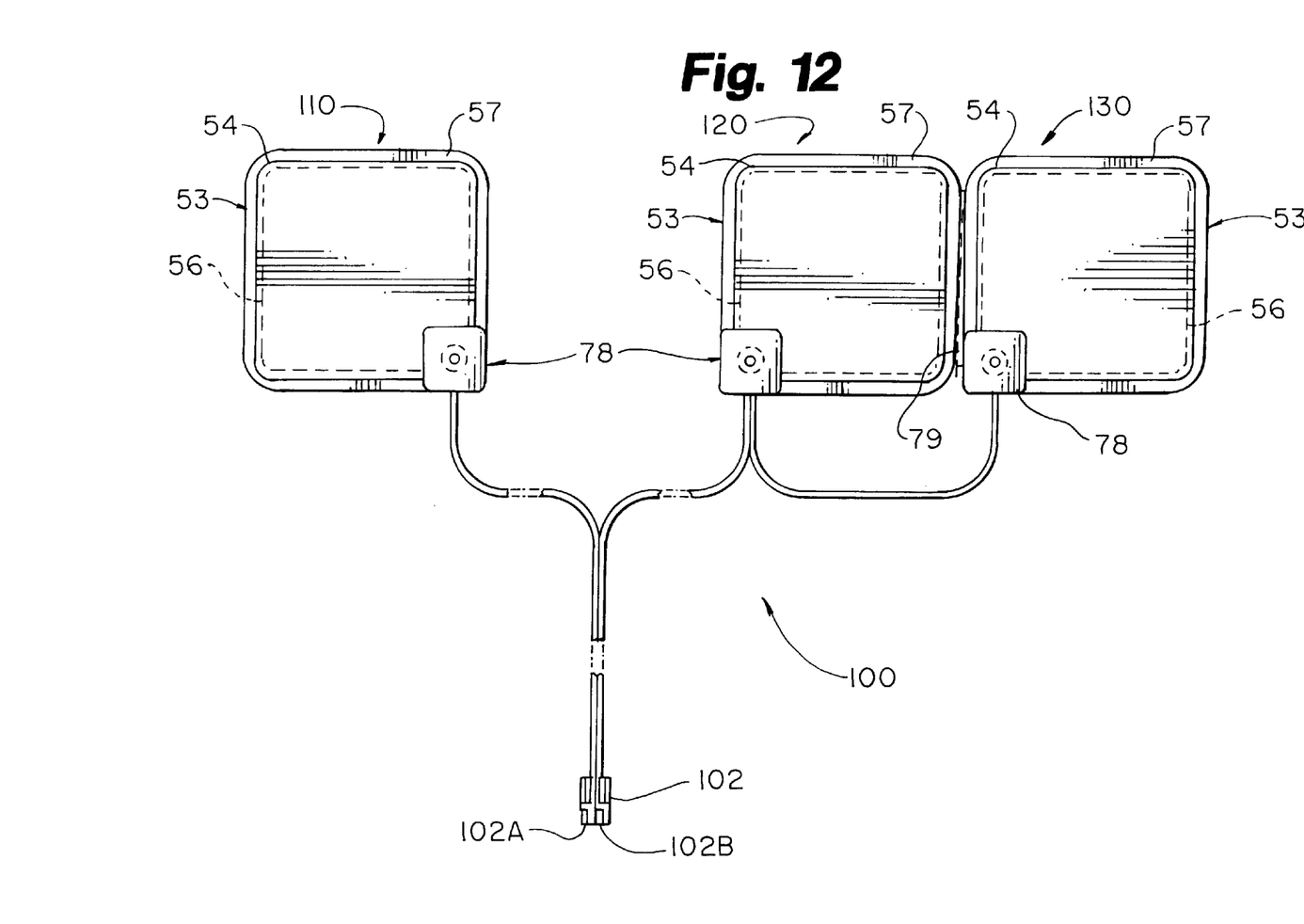
FIG. 12 is a plan view of another embodiment the electrode triad of the present invention with two of the electrodes being releasably joined.

Referring to FIG. 12, the electrodes 120, 130 of the triad 100 are releasably connected. In the embodiment depicted, the releasable connection is by perforations 79. Other means of releasably connecting the electrodes 120, 130 include, for example, a line of reduced thickness of the common backing layer 53 that facilitates tearing the two electrodes 120, 130 apart, a preformed crease in the common backing layer 53 that facilitates tearing the two electrodes 120, 130 apart, and releasable tape extending between the (not common) backing layer 53 of electrode 120 and the separate backing layer 53 of electrode 130. In the embodiment of FIG. 12, the electrodes 120, 130 may be applied to the patient as a single mated unit or the electrodes 120, 130 may be applied to the patient released from one another and spaced apart as depicted in FIG. 5.

Referring to the embodiments of FIGS. 3 and 12, electrode triad 100 includes a first electrode 110 which is electrically connected to electrical contact 102A in electrode connector 102. Electrode triad 100 also includes a second electrode 120 and a third electrode 130. Electrodes 120 and 130 are electrically connected to each other and to electrical contact 102B in electrode connector 102. Preferably, electrical contact 102A is coupled to the first electrical connector of AED connector 30 and electrical contact 102B is coupled to the second electrical connector of AED connector 30. The electrodes 110, 120, and 130 are made in substantial conformance to the description of electrode 50 in conjunction with FIG. 2. Accordingly, electrodes 110, 120, and 130 each include backing layer 53, patient engaging hydrogel layer 54, conductive portion 56, and insulating pad 78, as depicted in FIG. 2. As indicated above, the backing layer 53 may be common for electrodes 120, 130.

Figure 4:
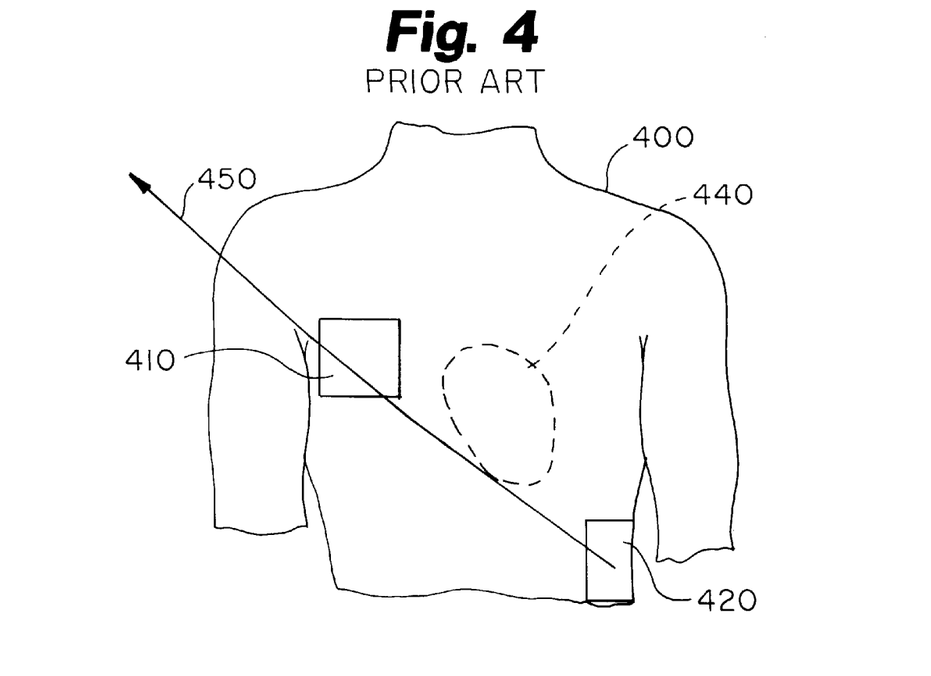
FIG. 4 is a plan view of a human chest with prior art electrodes applied.
Figure 6:
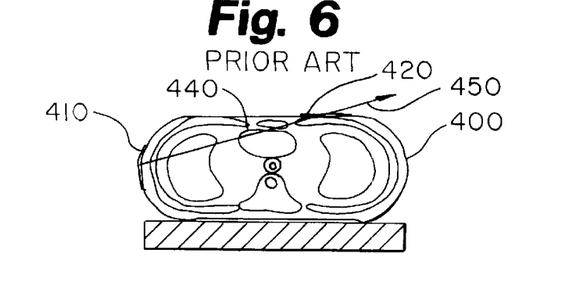
FIG. 6 is a sectional top view of a human chest with prior art electrodes applied thereto.

FIGS. 4 and 6 depict in FIG. 4 a human chest 400 is shown with prior art electrodes 410 and 420 applied. Electrodes 410, 420 may be formed as indicated above with reference to electrodes 50 of FIG. 2. The location of a human heart 440 is indicated in phantom. When a defibrillation shock is delivered, electrical current travels between electrodes 410 and 420. An arrow 450 illustrates the direction of the energy vector which results from a defibrillation shock.

FIG. 6 is a top planform sectional view of a human chest 400 of FIG. 4 with prior art electrodes 410 and 420 applied. Electrodes 410 and 420 are in the same positions shown in FIG. 4. The chest includes a human heart 440. The arrow 450 illustrates the direction of the energy vector which results from a defibrillation shock. It can be seen with reference to FIGS. 5 and 6 that it is difficult to have the energy vector 450 intersect the heart 440 when using only two electrodes 410, 420 of the prior art.

In FIG. 5 the human chest 400 is shown with the electrode triad 100 of the present invention applied. As shown in FIG. 5, first electrode 110 is positioned relatively low on the patient's left anterior side. Second electrode 120 is positioned relatively high on the front (anterior side) of the chest below the right shoulder. Third electrode 130 is positioned in a relatively mid position on the back (posterior side) of the chest below the left shoulder. It should be noted that since electrodes 120 and 130 are electrically connected, their positions are interchangeable. (e.g. in FIG. 5 the position occupied by electrode 120 could alternately be occupied by electrode 130.) Those skilled in the art will readily recognize that electrodes 110, 120, and 130 may be placed in other locations on a patient's body without departing from the spirit and the scope of this invention.

When a defibrillation shock is delivered, a portion of the shock current travels between electrode 120 and electrode 110. The remainder of the shock current travels between electrode 130 and electrode 110. An arrow 550A illustrates the direction of the energy vector which results from a defibrillation shock between electrode 130 and 110. An arrow 550B illustrates the direction of the energy vector which results from a defibrillation shock between electrode 120 and 110. An arrow 550R illustrates the direction of the resultant energy vector which results from the two vectors 550A and 550B. The resultant vector 550R passes through the center of the heart 440. It is important that the vector 550R pass through the myocardium of the heart 440 in order to make the likelihood of capture approximate 100 percent. If the myocardium of the heart 440 is less than 100 percent captured, there is a high probability of refibrillation of the heart 440 after delivery of the shocking energy. The electrode triad 100 of the present invention helps ensure 100 percent capture by delivering the energy through the center of the heart 440 to defibrillate the heart 440 and to minimize the chance of refibrillation.

Figure 7:
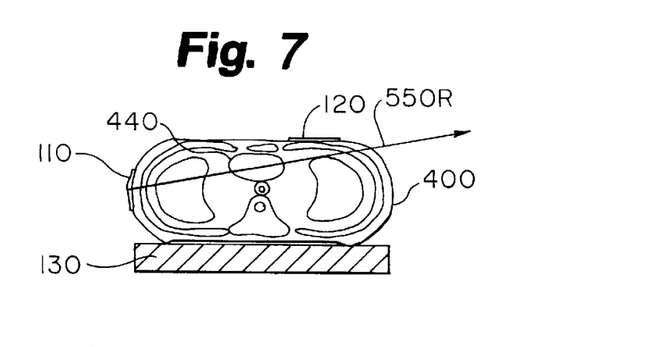
FIG. 7 is a sectional view of a human chest with the electrode triad of the present invention applied thereto.

FIG. 7 is a sectional view of a human chest 400 of FIG. 4 with the inventive electrode triad 100 applied. Electrodes 110, 120, and 130 are in the same positions shown in FIG. 5. The chest 400 includes a human heart 440. The arrow 550R illustrates the direction of the energy vector which results from a defibrillation shock and is the same vector as resultant energy vector 550R of FIG. 5. It should be noted that, as distinct from the energy vector 450 resulting from a defibrillation shock through the prior art electrodes 410 and 420 (FIGS. 4 and 6), a defibrillation shock delivered by the electrodes 110, 120 and 130 results in an energy vector 550R that passes centrally through the human heart 440. The energy vector 550R is more effective at returning the human heart 440 to normal rhythm from a stricken condition, as indicated above.

Figure 8:
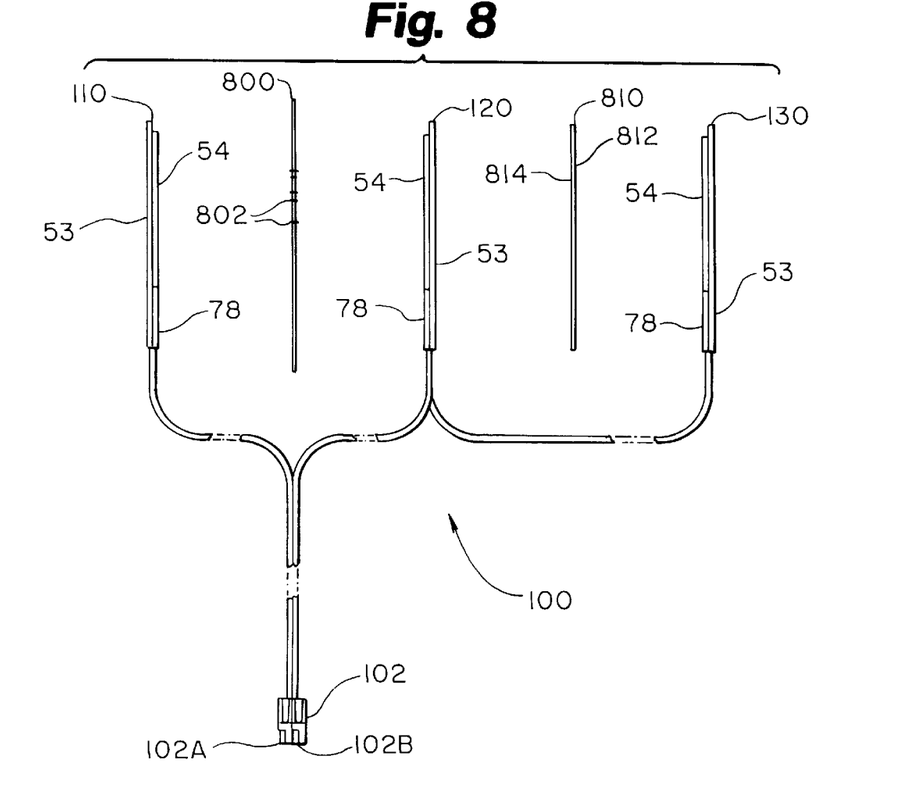
FIG. 8 is an exploded, plan view of a preferred packaging method for the electrode triad.

FIG. 8 is a plan view of electrode triad 100 which illustrates a preferred packaging configuration. For illustrative purposes the electrodes 110, 120, and 130 are separated from each other in exploded view format. The edges of electrodes 110, 120 and 130 are visible in FIG. 8. Each electrode includes backing layer 53, patient engaging hydrogel layer 54, and insulating pad 78.

When the electrode triad 100 is packaged, the patient engaging hydrogel layer 54 of electrode 110 faces the patient engaging hydrogel layer 54 of electrode 120. A release liner 800 is placed between electrode 110 and electrode 120. This release liner 800 is treated with a release agent on both sides so that the adhesive border 57, and the patient engaging hydrogel layer 54 of electrodes 110 and 120 will bond only lightly to release liner 800. Release liner 800 includes a number of small apertures 802 defined therein. The apertures 802 allow hydrogel layer 54 of electrode 110 and hydrogel layer 54 of electrode 120 to extrude therethrough, thereby making physical contact. This direct, physical hydrogel contact forms an electrical connection between electrode 110 and electrode 120. This electrical connection supports the automatic self test feature of AED 10 described above.

A second release liner 810 is adhesively attached to backing layer 53 of second electrode 120. When the electrode triad 100 is packaged, third electrode 130 is releasably attached to second release liner 810. A first side 812 of release liner 810 is treated with a release agent so that the adhesive coated border 57 and the patient engaging hydrogel adhesive layer 54 of electrode 130 will only bond lightly to release liner 810. A second side 814 of release liner 810 has a surface which is readily bonded with adhesives. A transfer adhesive is used to strongly bond release liner 810 to backing layer 53 of second electrode 120. A suitable transfer adhesive is commercially available from 3M Company of St. Paul, Minn. which identifies it as model 1524.

When electrode triad 100 is packaged in this manner conductive portion 56 and patient engaging hydrogel layer 54 of third electrode 130 are completely surrounded by electrically insulating materials. Adhesive coated backing layer 53 covers one surface of conductive portion 56. Adhesive coated backing layer 53 extends beyond the perimeter margins of both conductive portion 56 and hydrogel layer 54 to form adhesive coated border 57 (best shown in FIG. 3). Adhesive coated border 57 is releasably adhered to release liner 810 to provide electrical insulation around the edges of conductive portion 56 and hydrogel layer 54. Release liner 810 and backing layer 53 of second electrode 120 cover the remaining surface of conductive portion 56 and hydrogel layer 54.

This method of packaging gives the operator of AED 10 the option of using electrode triad 100 as an electrode pair in a manner similar to the noted prior art. When this method is used, first electrode 110 is placed on the right anterior side of the chest as shown in FIG. 5. Second electrode 120 is adhered on the left anterior side of the chest below the left shoulder (also as shown in FIG. 5). Third electrode 130 remains adhesively attached to release liner 810. Defibrillation shocks can now be delivered by AED 10. The safety of the AED operator is ensured by the electrically insulating materials which completely surround the conductive portions of third electrode 130.

Figure 13:
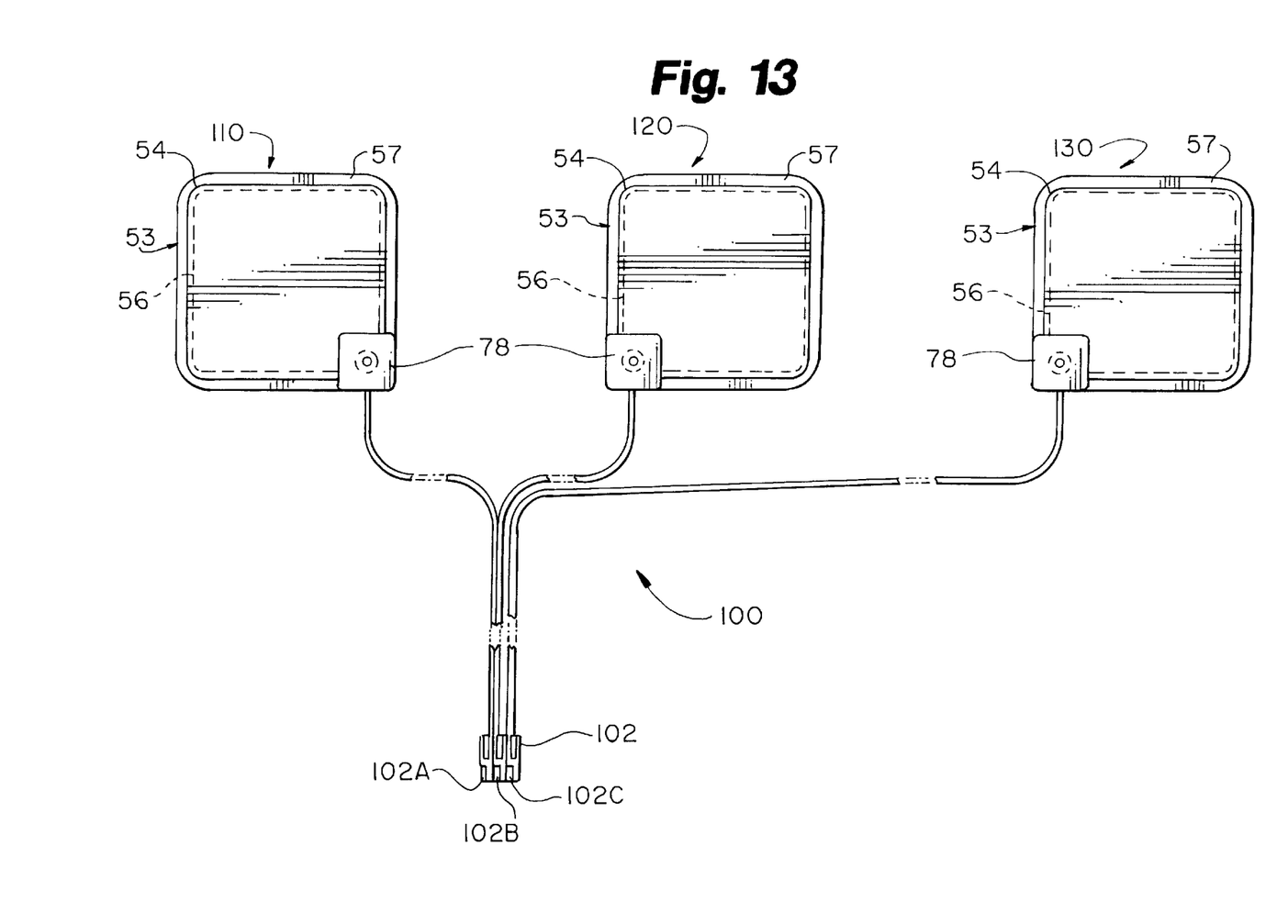
FIG. 13 is a plan view of another embodiment the electrode triad of the present invention with three independent connectors for connection to the AED.

FIG. 13 depicts a further embodiment electrode triad 100 of the present invention. In this case, the electrode triad 100 has substantially the same features as described above in reference to FIG. 3. The connector 102 has three connectors 102A, 102B, and 102C in communication with the electrodes 110, 120, and 130, respectively. To couple the triad 100 to the AED 10, the AED connector 30 must be modified to accept the three connectors 102A, 102B, and 102C. In the case that only two electrodes are desired to be applied to the patient, the connector 120C may not be plugged into the AED connector 30. This affords added safety to the operator of the AED 10 in that no charge will be sent to the electrode 130.

Figure 14:
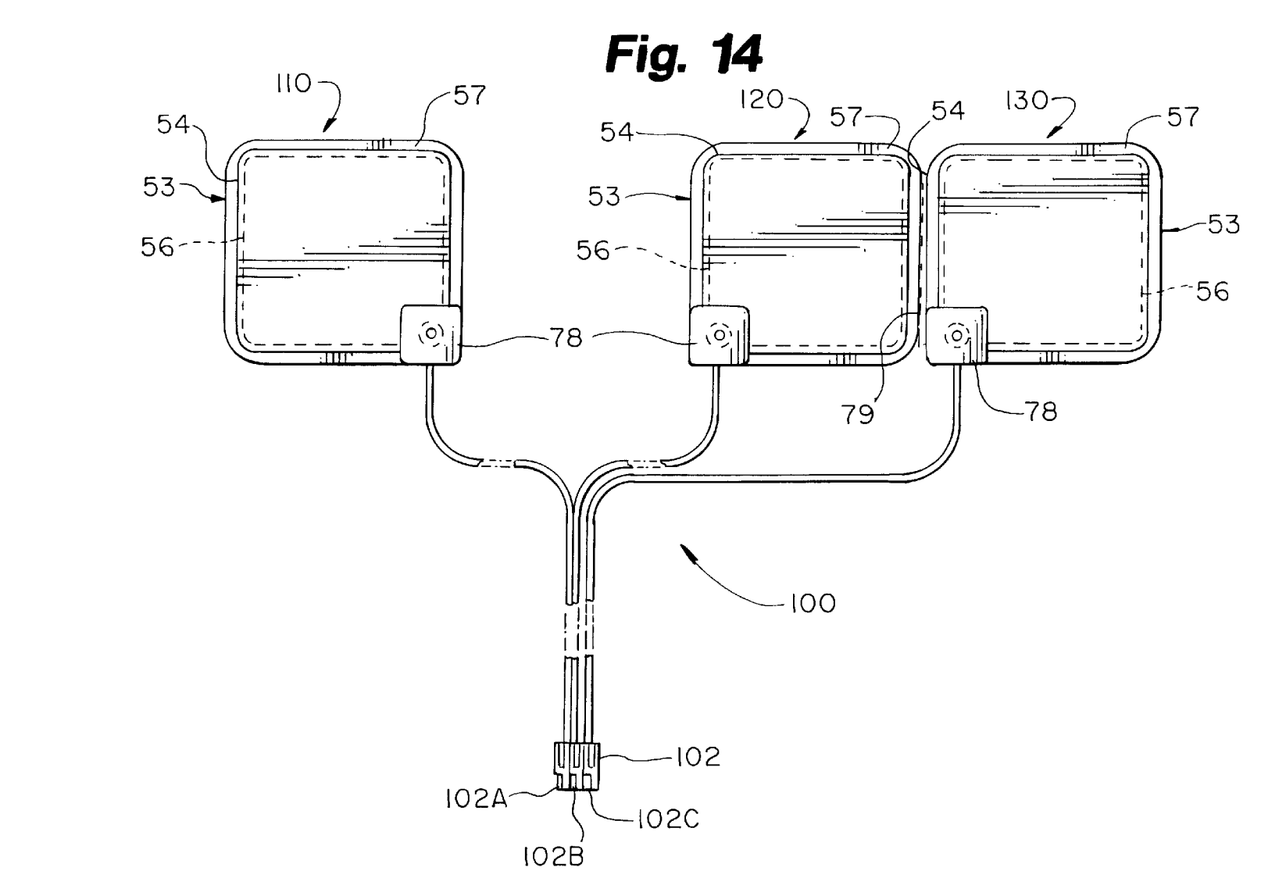
FIG. 14 is a plan view of another embodiment the electrode triad of the present invention with two of the electrodes being releasably joined and with three independent connectors for connection to the AED.

FIG. 14 depicts another embodiment electrode triad 100 of the present invention. In this case, the electrode triad 100 has substantially the same features as described above in reference to FIG. 13. In addition to those features, the electrode has a releasable connection as by perforations 79 formed in the common backing layer 53 as indicated in reference to FIG. 12. Like the embodiment of FIG. 12, electrodes 120, 130 may be applied to the patient as a connected unit (similar to the emplacements of FIG. 4) or may be separated and applied to the patient substantially as depicted in FIG. 5.

Figure 9:
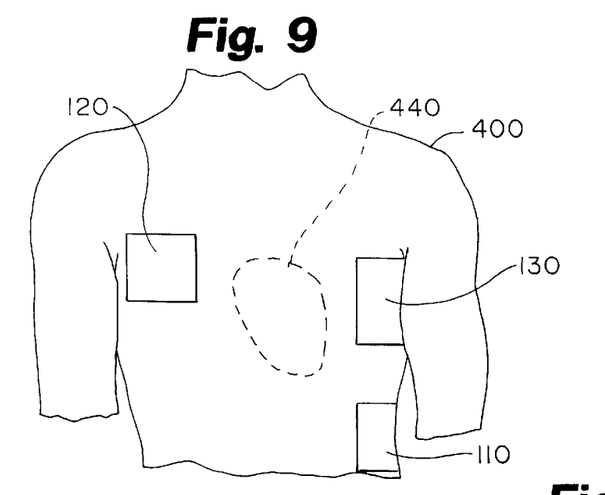
FIG. 9 is a plan view of a human chest with the electrode triad applied thereto.

Those skilled in the art will readily recognize that electrodes 110, 120, and 130 may be placed in locations on a patient's body other than those shown in FIG. 5. FIG. 9 is a plan view of human chest 400 illustrating alternate locations for electrodes 110, 120, and 130. In FIG. 9, electrode 130 is applied in a left axillary (lateral) position on chest 400.

Figure 10:
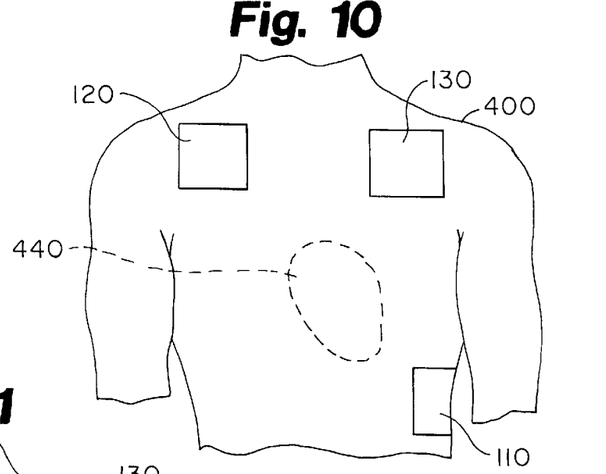
FIG. 10 is a plan view of a human chest with the electrode triad applied thereto.

FIG. 10 is a plan view of human chest 400 further illustrating alternate locations for electrodes 110, 120, and 130. In FIG. 10, electrode 130 is applied in a left infraclavicular (anterior) position on human chest 400.

Figure 11:
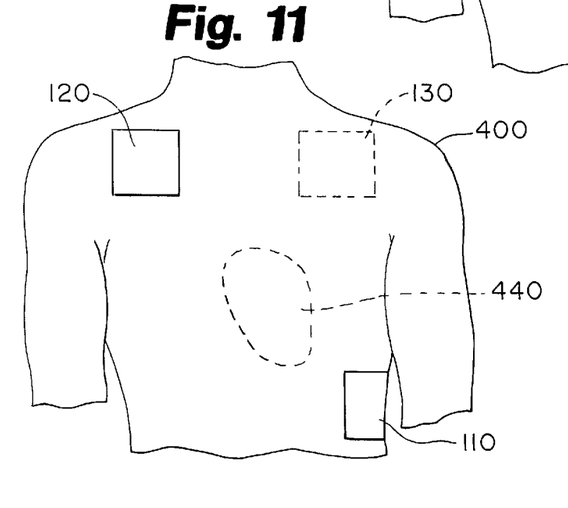
FIG. 11 is a plan view of a human chest with the electrode triad applied thereto.

FIG. 11 is a plan view of human chest 400 which again illustrates alternate locations for electrodes 110, 120, and 130. In FIG. 11, electrode 130 is applied in a left supraclavicular (posterior) position on human chest 400.

In operation, AED 10 is used for emergency treatment of victims of cardiac arrest and is typically used by first responders. After placement of the triad 100 on the victim, as indicated above, AED 10 preferably automatically analyzes a patient's cardiac electrical signal received from triad 100 and advises the user to shock the victim upon detection of: (1) ventricular fibrillation; (2) ventricular tachycardia; (3) other cardiac rhythms with ventricular rates exceeding 180 beats per minute and having amplitudes of at least 0.15 millivolts. When such a condition is detected, AED 10 will build up an electrical charge for delivery to the victim to defibrillate the victim's heart with a defibrillation shock. The operator of AED 10 is typically guided by voice prompts and the illuminated rescue switch 18. Activating rescue switch 18 discharges electrical energy through the electrodes 110, 120 and 130 of triad 100 developing the energy vector 550R through the heart 440. Olson, et al. U.S. Pat. No. 5,645,571 (incorporated herein by reference) discloses the general construction and manner of use of an AED 10.

The present invention may be embodied in other specific forms without departing from the spirit of the essential attributes thereof. Therefore, the illustrated embodiments should be considered in all respects as illustrative and not restrictive, reference being made to the appended claims rather than to the foregoing description to indicate of the scope of the invention.

What is claimed is:

1. An energy delivery system for use with an automatic external defibrillator (AED), the AED having a case containing a plurality of AED components, the AED components including at least a battery, a control system, a charge system, and an electrical connector, the battery electrically coupled to the control system, the control system communicatively coupled to the charge system, the charge system for generating a stored quantity of energy responsive to a communication from the control system, the control system selectively commanding a discharge of the stored energy to the electrical connector, the energy delivery system comprising:

three electrodes, each electrode being separable for making spaced apart electrical contact with a skin surface of a patient, each electrode being electrically connectable with the electrical connector for communicating the stored energy to the patient, each of the three electrodes having a patient engaging, electrically-conductive hydrogel layer;

a package, a first electrode of the three electrodes being maintained in the package, the package including a release liner substantially overlying the patient engaging, electrically-conductive hydrogel layer of the first electrode; and a second electrode and a third electrode of the three electrodes being maintained in the package, the package including a second release liner substantially interposed between the patient engaging, electrically-conductive hydrogel layers of the second electrode and the third electrode of the three electrodes.

2. The energy delivery system of claim 1 wherein the release liner substantially interposed between the patient engaging, electrically-conductive hydrogel layers of the second electrode and the third electrode of the three electrodes forms an electrical connection between the second electrode and the third electrode.

3. The AED of claim 2 wherein the first electrode and the second electrode are substantially electrically isolated when disposed in the package.

\* \* \* \* \*